(12) United States Patent
Schwartz

(10) Patent No.: US 7,909,781 B2
(45) Date of Patent: Mar. 22, 2011

(54) ULTRASONIC TREATMENT OF GLAUCOMA

(76) Inventor: Donald N. Schwartz, Long Beach, CA (US)

( * ) Notice: Subject to any disclaimer, the term of this patent is extended or adjusted under 35 U.S.C. 154(b) by 427 days.

(21) Appl. No.: 11/842,909

(22) Filed: Aug. 21, 2007

(65) Prior Publication Data

US 2008/0051681 A1    Feb. 28, 2008

Related U.S. Application Data

(60) Provisional application No. 60/839,473, filed on Aug. 22, 2006.

(51) Int. Cl.
*A61F 9/007* (2006.01)
*A61B 18/00* (2006.01)
*A61B 18/04* (2006.01)

(52) U.S. Cl. .................. 601/2; 606/27; 606/28
(58) Field of Classification Search .................. 601/2
See application file for complete search history.

(56) References Cited

U.S. PATENT DOCUMENTS

| | | |
|---|---|---|
| 4,350,917 A | 9/1982 | Lizzi |
| 4,484,569 A | 11/1984 | Driller |
| 4,531,934 A | 7/1985 | Kossovsky |
| 4,561,019 A | 12/1985 | Lizzi |
| 4,729,373 A | 3/1988 | Peyman |
| 4,858,124 A | 8/1989 | Lizzi |
| 5,080,101 A | 1/1992 | Dory |
| 5,209,221 A | 5/1993 | Riedlinger |
| 5,458,130 A | 10/1995 | Kaufman |
| 6,039,689 A | 3/2000 | Lizzi |
| 6,162,193 A | 12/2000 | Ekberg |
| 6,352,519 B1 | 3/2002 | Anis et al. |
| 6,416,740 B1 | 7/2002 | Unger |
| 6,433,464 B2 * | 8/2002 | Jones ........................ 310/328 |
| 6,652,459 B2 | 11/2003 | Payne |
| 6,679,855 B2 | 1/2004 | Horn |
| 6,685,657 B2 | 2/2004 | Jones |
| 6,764,439 B2 | 7/2004 | Schaaf |
| 6,979,328 B2 | 12/2005 | Baerveldt |
| 7,094,225 B2 | 8/2006 | Tu |
| 2002/0111608 A1 | 8/2002 | Baerveldt |
| 2003/0088260 A1 | 5/2003 | Smedley |

(Continued)

FOREIGN PATENT DOCUMENTS

FR    2631545 A1    11/1989

(Continued)

OTHER PUBLICATIONS

Extended European Search Report dated Sep. 10, 2009, which includes the supplementary European search report and the European search opinion, for related European Application No. 07814316.1.

(Continued)

*Primary Examiner* — Roy D Gibson
*Assistant Examiner* — Kaitlyn E Helling
(74) *Attorney, Agent, or Firm* — Jeffer Mangels Butler & Mitchell LLC

(57) ABSTRACT

A method of treating glaucoma is described herein. The method includes the steps of providing an ultrasonic device that emits ultrasonic energy, holding the ultrasonic instrument at a location external to the trabecular meshwork, transmitting the ultrasonic energy at a frequency to a desired location for a predetermined time, dislodging material built up in the trabecular meshwork, and generating heat that initiates biochemical changes in the eye.

11 Claims, 6 Drawing Sheets

U.S. PATENT DOCUMENTS

| | | | |
|---|---|---|---|
| 2003/0097151 A1* | 5/2003 | Smedley et al. | 607/2 |
| 2004/0030269 A1 | 2/2004 | Horn | |
| 2004/0091541 A1* | 5/2004 | Unger | 424/486 |
| 2006/0047263 A1* | 3/2006 | Tu et al. | 604/521 |
| 2006/0106370 A1 | 5/2006 | Baerveldt | |
| 2006/0106424 A1 | 5/2006 | Bachem | |
| 2006/0173437 A1 | 8/2006 | Robin | |
| 2006/0217741 A1 | 9/2006 | Ghannoum | |

FOREIGN PATENT DOCUMENTS

| | | |
|---|---|---|
| WO | WO2006/021651 A1 | 3/2006 |

OTHER PUBLICATIONS

Alexander JP, Acott TS; Involvement of protein kinase C in TNFalpha regulation of trabecular matrix metalloproteinases and TIMPs; Invest Ophthalmol Vis Sci. Nov. 2001; 42(12):2831-8.

Fleenor DL, Pang IH, Clark AF; Involvement of AP-1 in interleukin-1alpha-stimulated MMP-3 expression in human trabecular meshwork cells; Invest Ophthalmol Vis Sci. Aug. 2003;44(8):3494-501.

Office Action issued on May 25, 2010, by Chinese Intellectual Property Office in related Chinese Patent Application No. 200780035161.2.

Cellular Tolerance to Pulsed Hyperthermia, by D. M. Simanovskii, et al., Physical Review, Jul. 24, 2006.

Effect of Ultraviolet Irradiation Upon the Cutaneous Pain Threshold, by M. Lipkin, et al., Journal of Applied Physiology May 1955 vol. 7 No. 6; pp. 683-687.

"Cytokine induction by 41.8° C whole body hyperthermia 'WBH,'" by H. Ian Robins, et al., Cancer Letters, vol. 97, Issue 2, Nov. 6, 1995, pp. 195-201.

Stress Induced Changes in Lymphocyte Subpopulations and Associated Cytokines During Whole Body Hyperthermia of 41.8-42.2° C, by O. Ahlers, et al., Eur J Appl Physiol (2005) 95: 298-306.

Heat Shock Proteins and Regulation of Cytokine Expression, by Y. Xie, C.M. Cahill, A. Asea, P.E. Auron, and S.K. Calderwood, Infectious Diseases in Obstetrics and Gynecology 7:26-30 (1999).

Effects of Local and Whole Body Hyperthermia on Immunity by Gian Franco Baronzio, et al., Madame Curie Bioscience Database [Internet], Austin (TX): Landes Bioscience; 2000. [On the Internet at http://www.ncbi.nlm.nih.gov/books/NBK6083/].

Heat Shock Co-Activates Interleukin-8 Transcription, by Ishwar S. Singh, et al., Am J Respir Cell Mol Biol, Aug. 2008; 39(2): 235-242.

Alexander JP, Acott TS; Involvement of the Erk-MAP kinase pathway in TNFalpha regulation of trabecular matrix metalloproteinases and TIMPs; Invest Ophthalmol Vis Sci. 2003 Jan; 44(1):164-9.

Wang N, Chintala SK, Fini ME, Schuman JS; Ultrasound activates the TM ELAM-1/IL-1/NF-kappaB response: a potential mechanism for intraocular pressure reduction after phacoemulsification; Invest Ophthalmol Vis Sci. May 2003; 44(5):1977-81.

Bradley JM, Anderssohn AM, Colvis CM, Parshley DE, Zhu XH, Ruddat MS, Samples JR, Acott TS; Mediation of laser trabeculoplasty-induced matrix metalloproteinase expression byIL-1 and TNF; Invest Ophthalmol Vis Sci. 2000; 41:422-430.

Hosseini M, Rose AY, Song K, Bohan C, Alexander JP, Kelley MJ, Acott TS; IL-1 and TNF induction of matrix metalloproteinase-3 by c-Jun N-terminal kinase in trabecular meshwork; Invest Ophthalmol Vis Sci. Apr. 2006; 47(4):1469-76.

Pang IH, Hellberg PE, Fleenor DL, Jacobson N, Clark AF; Expression of matrix metalloproteinases and their inhibitors in human trabecular meshwork cells; Invest Ophthalmol Vis Sci. Aug. 2003; 44(8):3485-93.

Kelley MJ, Rose A, Song K, Lystrup B, Samples JW, Acott TS; p. 38 MAP kinase pathway and stromelvsin regulation in trabecular meshwork cells; Invest Ophthalmol Vis Sci. Jul. 2007; 48(7):3126-37.

Kelley MJ, Rose AY, Song K, Chen Y, Bradley JM, Rookhuizen D, Acott TS; Synergism of TNF and IL-1 in the induction of matrix metalloproteinase-3 in trabecular meshwork; Invest Ophthalmol Vis Sci. Jun. 2007; 48(6):2634-43.

Written Opinion issued in related Singapore Application No. 200901271-7, provided by the Austrian Patent Office as Search and Examination Authority, with a mailing date of May 19, 2010.

Bradley, John M.B., et al., "Effects of Mechanical Stretching on Trabecular Matrix Metalloproteinases", Investigative Ophthalmology & Visual Science, Jun. 2001, vol. 42 No. 7.

* cited by examiner

ULTRASONIC TREATMENT OF GLAUCOMA

This application claims the benefit of U.S. Provisional Application No. 60/839,473, filed Aug. 22, 2006, which is herein incorporated by reference in its entirety.

FIELD OF THE INVENTION

The present invention relates generally to the treatment of glaucoma and, more particularly, to a method for treatment of glaucoma using, low intensity ultrasonic energy.

BACKGROUND OF THE INVENTION

Open angle glaucoma exists when the pressure in the eye is not tolerated by the patient and is causing damage to the optic nerve. The current treatment for open angle glaucoma is aimed at reducing the intraocular pressure to a level that is safe for the patient's eye, to preserve vision.

Open angle glaucoma is treated with pharmaceutical agents. Another method of treatment, laser treatment for open angle glaucoma, has been reserved for medical treatment failures but is gaining some favor as a primary treatment. Another approach, intraocular surgery, is reserved for medical and/or laser failures.

Frequently, the increased pressure in the eye is caused by a blockage in the ability of the fluid to leave the eye, not an actual increase of the fluid itself. As shown in FIG. 1, the blockage is typically in the part of the trabecular meshwork near Schlemm's canal, called the juxtacanalicular meshwork. The meshwork is typically blocked by anatomical changes, pigment, extracellular matrix debris or pseudoexfoliative material.

Medical treatment is directed at decreasing the production of the fluid (aqueous humor) or enhancing the ability of the fluid to leave the eye. Medical treatment is not curative. It is used on a continuing basis to decrease the pressure. But, when the treatment is stopped the pressure rises. Also, medical treatment demands patient compliance, has unwanted side effects, is expensive, and may interact poorly with other medical care for the patient.

Laser treatment has been partially successful in its original (argon) method. Newer laser treatment, such as selective laser trabeculoplasty, is gaining favor. However, laser treatment is performed on the inside of the eye and treats the inner, not the outer, trabecular meshwork. With this treatment, there is a secondary physiologic response that causes cells to remove some debris after the laser is performed.

Frequently, after modern day cataract surgery there is a decrease in the intraocular pressure as an unintended positive side effect. When the lens is removed there is more space in the front of the eye. Typical modern cataract surgery removes the cataract by ultrasonic emulsification of the lens material. This method is known as phacoemulsification. Older cataract surgery, without implants, removed more material from inside the eye, but the decrease in intraocular pressure was not as consistent as with modern day or current surgery. It is believed that the ultrasound used to break up the lens material helps dislodge the built up material. However, this is just a side effect, and, as described below, the ultrasonic energy used in phacoemulsification is intense enough to damage tissue.

Accordingly, a need exists for a treatment of glaucoma that includes a method of applying ultrasonic energy to the eye to dislodge built up material and initiate biochemical processes to reduce and remove extracellular debris, thereby decrease pressure, and that can be performed without damaging tissue.

SUMMARY OF THE PREFERRED EMBODIMENTS

In accordance with a first aspect of the present invention, there is provided a method of treating glaucoma. The method includes the steps of providing an ultrasonic device that emits ultrasonic energy, holding the ultrasonic instrument at a location external to the trabecular meshwork, transmitting the ultrasonic energy at a frequency to a desired location for a predetermined time, dislodging material built up in the trabecular meshwork, and generating heat that initiates biochemical changes in the eye. In a preferred embodiment, the tip is rounded or the tip includes a curved corneal surface, a curved scleral surface and a ridge.

In accordance with another aspect of the present invention, there is provided a handheld ultrasonic device that includes a casing, an ultrasonic transducer disposed in the casing, a power supply, a rod extending from the ultrasonic transducer, and a tip located at the end of the rod. Ultrasonic energy is transferred from the ultrasonic transducer to the tip. In a preferred embodiment, the casing is attached to the ultrasonic transducer at a null point.

In accordance with another aspect of the present invention, there is provided a method of treating glaucoma in a human eye that includes an intraocular lens with an exterior surface, a cornea, a sclera, and a trabecular meshwork. The method includes the steps of implantation of the intraocular lens, providing an ultrasonic device that emits ultrasonic energy, holding the ultrasonic device at a location spaced from the intraocular lens, transmitting the ultrasonic energy at a frequency to a desired location for a predetermined time, dislodging material built up in the trabecular meshwork, and generating heat that initiates biochemical changes within the eye.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Described herein are preferred embodiments of a method for the ultrasonic treatment of glaucoma. The method includes the use of tools that are also shown in FIGS. 3-6.

Generally, the method includes providing ultrasonic energy to a desired area of the eye to dislodge material from the trabecular meshwork, thereby lowering the pressure within the eye. The presently described methods are used to reduce the pressure build up in the eye described above.

It will be appreciated that terms such as "front," "back," "top," "bottom," "side," "upwardly" and "downwardly" used herein are merely for ease of description and refer to the orientation of the components as shown in the figures. It should be understood that any orientation of the instruments and the components thereof described herein is within the scope of the present invention.

Figure 2:
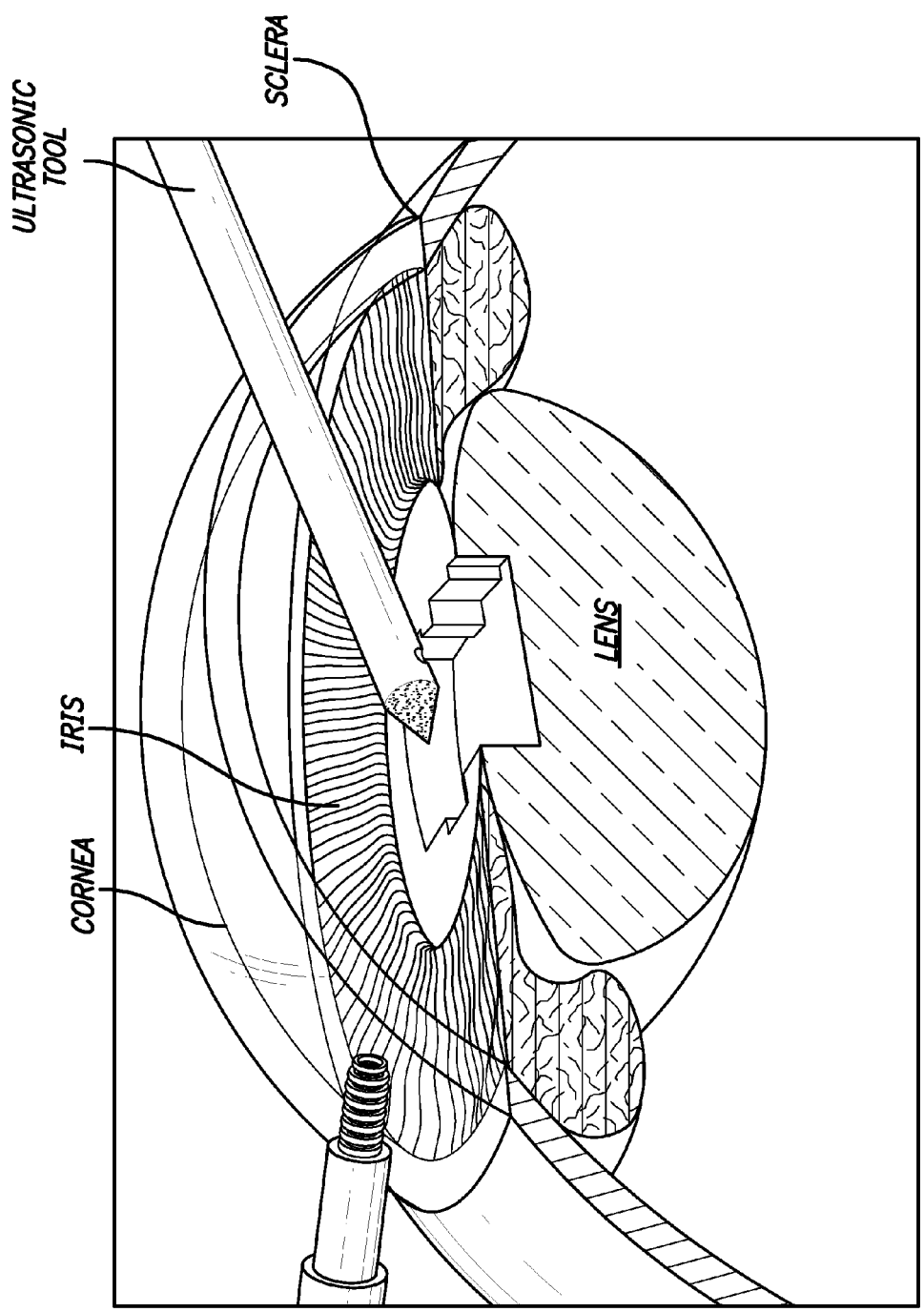
FIG. 2 is a view of a portion of the inside of an eye that includes instruments used in phacoemulsification.

FIG. 2 shows phacoemulsification being performed on an eye. As is described, the technique of phacoemulsification has been shown to cause a decrease of pressure in the eye. However, the ultrasound intensity used in phacoemulsification is quite vigorous and is designed to carve the lens tissue or disrupt its anatomy. As can be seen in FIG. 2, the instrument is actually in contact with the lens. In addition, the commonly used ultrasound instrument for phacoemulsification has a tip that is pointed and sharp, is designed to engage the tissue in the eye directly and has three inputs for ultrasound, irrigation and aspiration.

In a preferred embodiment of the present invention, the instruments (described below) focus the energy of the ultrasound a distance from the tissue and do not engage it directly. Moreover, the ultrasound intensity is preferably significantly less vigorous than phacoemulsification and, therefore, creates acoustic energy at a much gentler intensity. Lastly, the specific area and focus of the treatment is the trabecular meshwork in the anterior portion of the globe, and not the crystalline lens of the eye, as in phacoemulsification.

The forces obtained from ultrasound treatment are complex, but fit into two main categories: sonomechanical and heat generated. For example, see U.S. patent application Ser. No. 11/220,128 to Bachem and U.S. Pat. No. 6,162,193 to Ekberg, the entireties of which are incorporated herein by reference. Ultrasound creates microbubbles which may implode vigorously and thereby create heat and violent micromovement. This is known as cavitation. This creation of microbubbles and subsequent implosion with heat is either stable or unstable (transient). The stable cavitation is less likely to lead to cell necrosis and tissue damage. In addition there is an effect of the wavefront of the ultrasound that creates a phenomenon of streaming that allows the movement of particles within a fluid.

The device 10 for the treatment of glaucoma by ultrasound described below includes a balance such that the frequency, power and duration of the propagated ultrasound has the optimum balance of controlled cavitation, heat and acoustic streaming to effect the trabecular meshwork. The effect is such that debris, or other occlusive structures, may be dislodged to create a larger outflow by the forces mentioned above. In addition the nature of the heat generated and the subsequent inflammatory reaction is directed to initiating cascades of biochemical reactions that lead to remodeling of the extracellular matrix and induction of macrophages to remove extracellular debris to further enhance the long term effect of the treatment.

Described herein are two types of instruments used for ultrasonically treating the eye, one for immediately after cataract surgery (intraocular), and one for use on the surface of the eye (external), which can be used without having to enter the interior of the eye.

Figure 3:
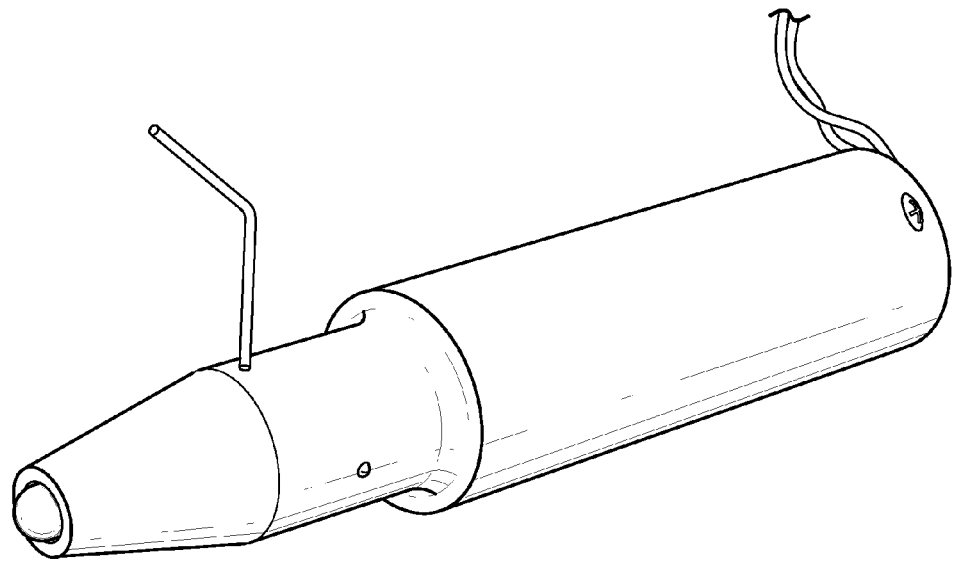
FIG. 3 is a perspective view of an ultrasonic device used for treatment of glaucoma that is used external of the eye, in accordance with a preferred embodiment of the present invention.
Figure 4:
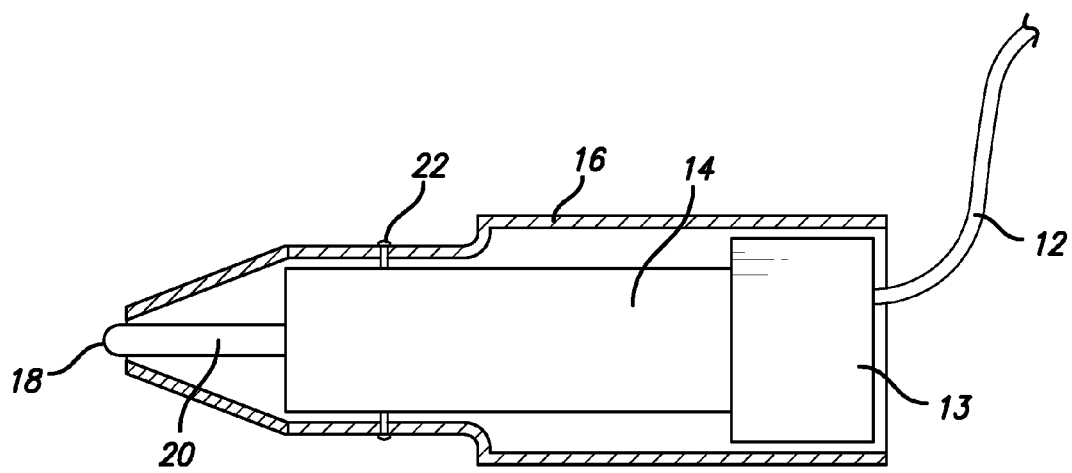
FIG. 4 is a cross-sectional side elevational view of the device of FIG. 3.
Figure 5:
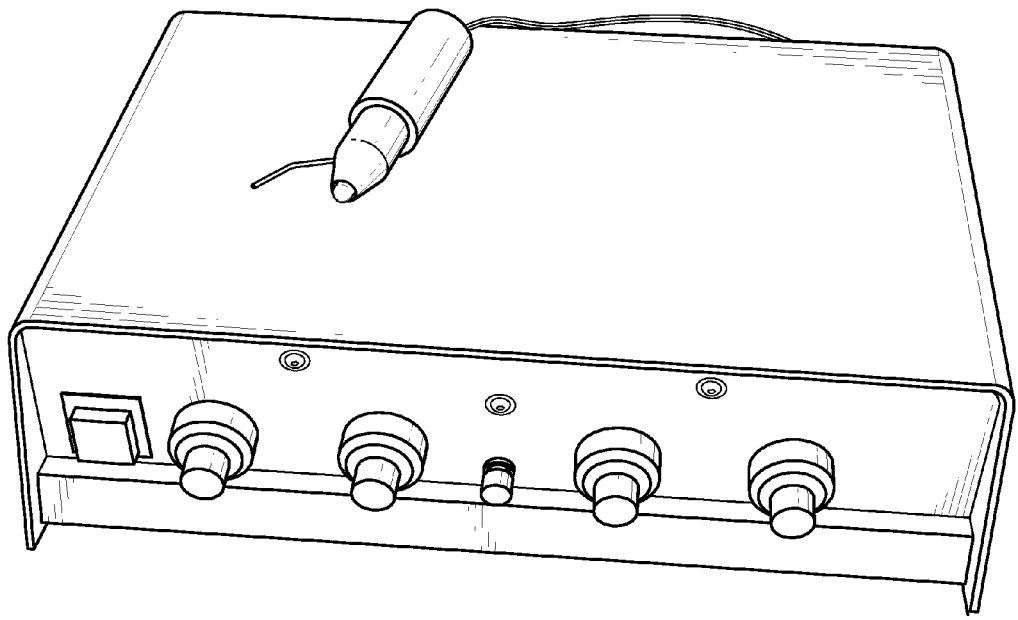
FIG. 5 a perspective view of the ultrasonic device of FIG. 3 along with a power supply.

Referring to FIGS. 3-5, a device or probe 10 for treatment on the outside surface of the eye is shown. Generally, the device 10 includes a power cord 12, a power supply 13 and an ultrasonic transducer 14 housed within a casing 16. It is contemplated that either AC or DC power can be used. However, in a preferred embodiment, DC power is provided (which may be from alternating current and then converted to DC or it may be from a battery pack). It will be understood by those skilled in the art that the type of ultrasonic transducer is not a limitation on the present invention. For example, the ultrasonic energy can be provided by piezoelectrics, liquids, crystals, etc. See, for example, U.S. Pat. No. 6,616,030 to Miller, which is incorporated by reference in its entirety herein. In the example shown in the figures, the ultrasonic transducer 14 uses piezoelectric technology. The ultrasonic energy produced by the transducer 14 is transmitted down a rod 20 and to the tip 18. Preferably, the tip 18 is smooth and rounded with a surface that allows for appropriate gel or liquid interface to the ocular surface. The smooth tip is preferred over the sharp tip of the prior art to prevent laceration of the exterior ocular surface or the cornea.

In a preferred embodiment, the casing 16 is attached to the transducer at a null point so as to not upset, or diminish ultrasound production within the casing; but avoiding contact with the tip to 18 allow maximum energy. As shown in FIG. 4, there is a space between the casing 16 and rod 20 and/or tip 18. The casing 16 can be attached to the transducer, for example, by threaded fasteners 22, rivets or the like.

As shown in FIGS. 3-5, the casing 16 has is shaped so that it fits easily into a user's hand. In a preferred embodiment, the casing 16 includes a handle 24 extending therefrom that can be grasped by a user's second hand. With this design the user can grasp the casing 16 with one hand and use the other hand to guide the device 10 using the handle 24. This provides a greater ability to manipulate the device 10 as desired. The handle 24 may be straight or bent (as is shown in FIG. 3). The casing 16 may also include a depression or depressions therein or other ergonomic additions to make the casing 16 easier to grip.

In an exemplary embodiment, the instrument is 9 cm long from the back of the casing to the tip and the tip is rounded to approximately a 4 mm diameter. However, this is not a limitation on the present invention.

Figure 4A:
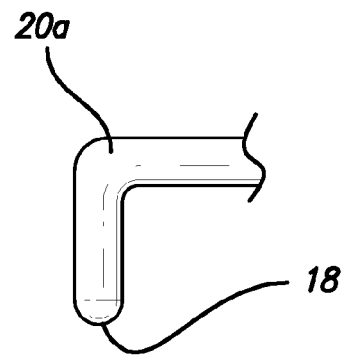
FIG. 4a is a side elevational detail of the tip of the device of FIG. 3 with a bent rod.

As shown in FIG. 4, in a preferred embodiment, the rod 20 is straight. However, in another embodiment, the rod 20 can be bent at an angle. As shown in FIG. 4a, the angle can be about 90 degrees. However, the angle can also be between 0 and 90 degrees. The ultrasonic energy is transmitted directly to the tip 18 and with the straight rod 20 provides movement in a forward and backward direction (like a piston or jackhammer). The rod 20a bent at a 90 degree angle provides for motion that is parallel to the axis of the rod and causes a back and forth sliding movement at the tip 18.

Figure 4B:
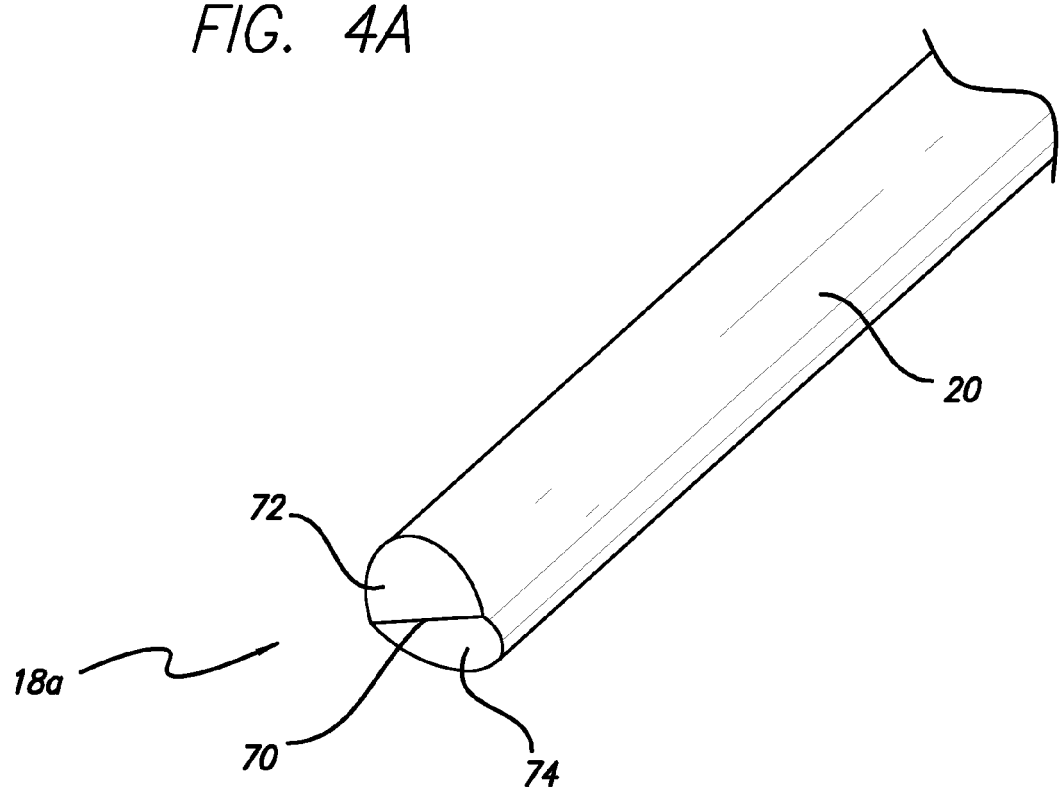
FIG. 4b is a perspective view of another embodiment of the tip.
Figure 4C:
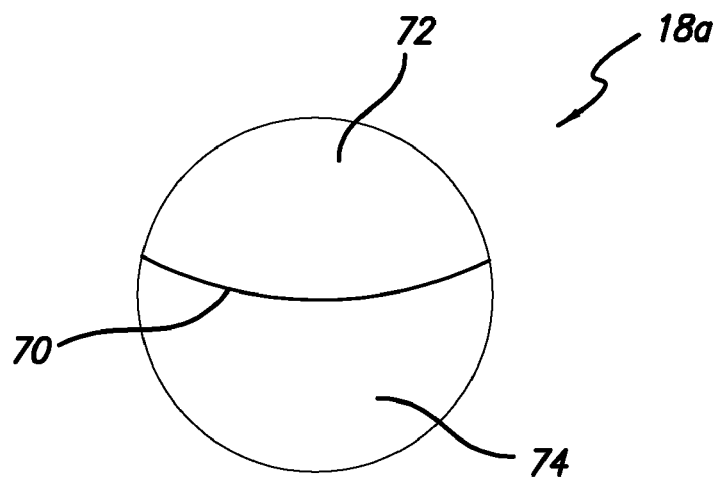
FIG. 4c is an end view of the tip of FIG. 4b.
Figure 4D:
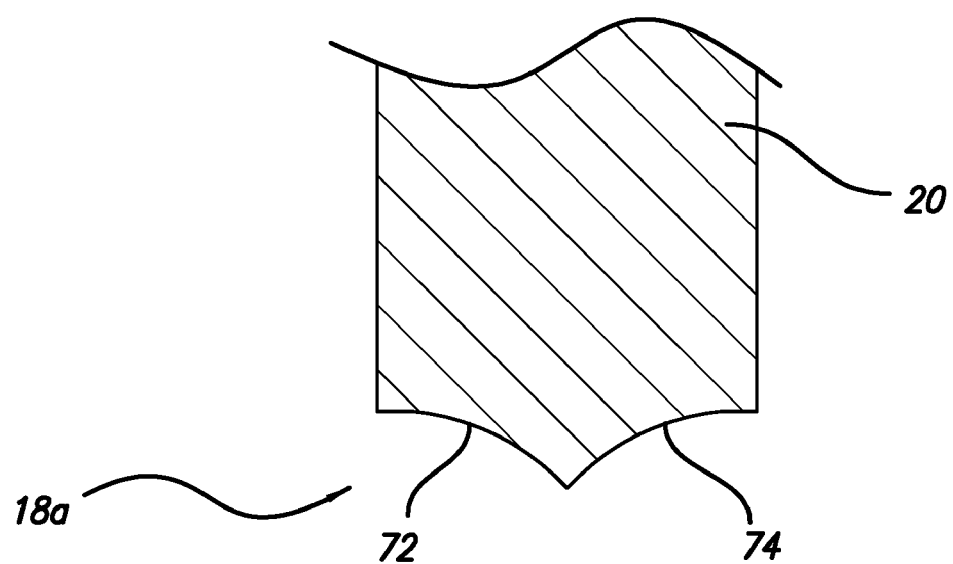
FIG. 4d is a cross-sectional side elevational view of the tip of FIG. 4b.

Referring to FIGS. 4b-4d, as will be appreciated by those skilled in the art, the cornea and sclera both have a different radius of curvature. As a result, an angle is formed where they join (see FIG. 2). As shown in FIGS. 4b-4c, in another embodiment, the tip 18a can be shaped so as to fit into or engage the junction of the cornea and sclera (known as the limbus). As shown in FIG. 4c, tip 18a includes a ridge 70, a corneal section 72 and a scleral section 74. The radius of curvature of the corneal section 72 and scleral section 74 mimics that of the typical cornea and sclera. As is shown in FIG. 4c, the ridge 70 has a slight curvature to it to match the natural curve of the cornea. In use, the ridge 70 is placed at the junction of the cornea and sclera (at the limbus) and the corneal section 72 rests against the cornea and the scleral section rests against the sclera. It will be understood that the ridge 70, corneal section 72 and scleral section 74 have smooth and rounded edges so as to prevent damage to the eye.

In an alternative embodiment, the tip may include a heating element that allows the heat created by the ultrasound energy to be enhanced. As is known in the art, tissue necrosis and pain are initiated at approximately 42.5 degrees centigrade. As is mentioned above, it is desirable to heat the target tissue enough to cause favorable biochemical processes. Accordingly, the heating element can be provided to heat the tissue to a level favorable to provide the biochemical processes described above, but below a level that creates tissue necrosis and pain.

Figure 1:
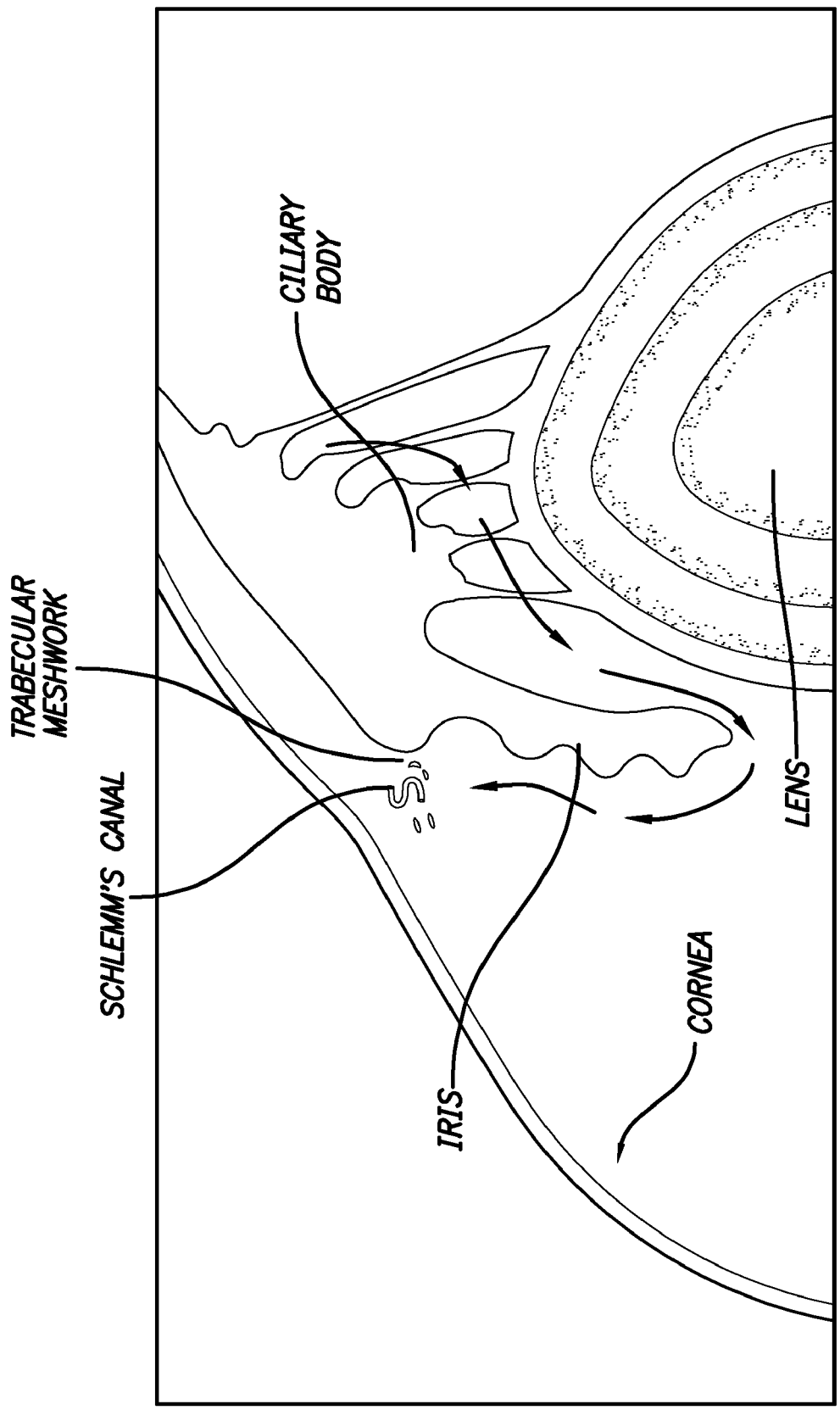
FIG. 1 is a view of a portion of the inside of an eye.

With reference to FIGS. 1 and 2 for the anatomy of the eye and FIG. 3, in use, the device 10 is used to apply directed or focused ultrasound to the area overlying the meshwork. In another embodiment, the ultrasonic energy may be unfocused. For example, focused ultrasound can be applied at 63,500 Hz using 4 watts of power. As can be seen in FIG. 2, the meshwork is located near the area where the cornea and sclera meet. Preferably, anesthetic and/or conduction gel or liquid is placed on the eye (or on the tip 18) and then ultrasonic acoustic energy is applied at the desired frequency, which in turn is transmitted to the trabecular meshwork, thereby dislodging material that is blocking fluid passage and heating the meshwork to initiate heat shock proteins, stimulate matrix metalloproteinase and induce macrophage activity and/or other desired biochemical processes.

In operation, the device 10 is moved 360° around the eye over the limbal area, while providing ultrasonic energy to the eye. However, in a preferred embodiment, the tip 18 is not swept around the limbal area of the eye in a 360° path, but instead, the user stops at a number of predetermined points and applies the ultrasonic energy at a predetermined frequency, for a predetermined duration and at a predetermined power. For example, the user may stop at twelve equally spaced points similar to the hours on a clock. In another embodiment, with an approximately 4 mm tip, only eight treatment areas may be sufficient.

The length of time, the number of treatment areas and the intensity of the ultrasound energy depend on individual cases. In an exemplary embodiment, the procedure may be performed at about 63,500 Hz with 4 watts of power for about twenty second intervals at about twelve points around the eye. However, these numbers are not a limitation on the present invention. Also, in some cases it may be necessary that after such treatment that anterior corneal massage is performed to help flush aqueous humor though the meshwork to help clear the pathway.

In operation, the ultrasonic energy is provided as follows. In a preferred embodiment, the frequency range of the ultrasonic energy is about 20,000 to 100,000 Hz. In a more preferred embodiment, the frequency range is from about 50,000 to 70,000 Hz. In a most preferred embodiment, the frequency range is from about 62,000 to 66,000 Hz. In a preferred embodiment, the duration range is about 5 to about 35 seconds. In a more preferred embodiment, the duration range is about 12 to about 27 seconds and in a most preferred embodiment, the duration range is about 18 to about 22 seconds. In a preferred embodiment, power is provided in the range of about 1 to about 6 watts, with about 4 watts being most preferred. As is described above, these ranges will be different for individual cases and therefore, these are not a limitation on the present invention.

These ranges are low intensity enough to prevent damage to the eye. However, in a preferred embodiment, the ultrasonic energy applied to the structures of the eye generates heat and sonomechanical acoustic streaming or stable cavitation that is transmitted to the meshwork and helps dislodge the built up material, and initiates biochemical changes to restructure the extracellular matrix and induce macrophage activity as described above.

In a preferred embodiment, to prevent contamination or spread from one patient to another, the exposed tip 18 or 18*a* of the device 10 can be covered with a small finger cot or condom. With such a cover over the tip there is little or no decrease in the treatment temperature rise than when the treatment is performed without a condom or the like.

Figure 6:
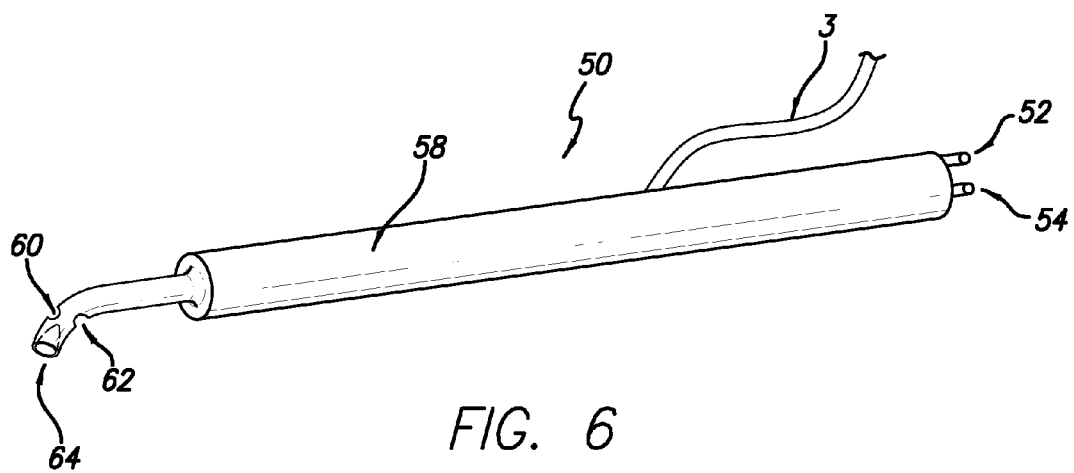
FIG. 6 is a side elevational view of an ultrasonic device used for treatment of glaucoma that is used intraocularly, in accordance with another preferred embodiment of the present invention.

Referring to FIG. 6, a device for treatment inside the eye is shown. This device is preferably used after cataract surgery since entry into the interior of the eye has already been made. However, this is not a limitation on the present invention. During cataract surgery the crystalline lens is replaced with an intraocular lens. The intraocular device 50 is for treatment within the eye. As described above, there is typically a decrease in pressure in the eye after cataract surgery.

The intraocular device 50 preferably includes attachment ports 52 and 54 for introduction of the irrigation fluid and aspiration of the irrigation fluid, respectively. However, it is contemplated that ports 52 and 54 can be omitted in an embodiment.

The intraocular device 50 also includes a power supply cord 56 for the transducer module (similar to the one in device 10) of the ultrasound, which is housed in a handpiece 58.

Located at an end of handpiece 58 opposite the end of attachment ports 54 and 56 is a tip 64 that preferably includes ports 60 and 62 that allow for the inflow of the fluid from attachment port 52 and into and out of the eye respectively.

The tip 64 is designed acoustically with the appropriate concavity or convexity to allow the focusing of the ultrasound into the trabecular meshwork. It may also be unfocused ultrasonic energy. In a preferred embodiment, the tip 64 includes an inverted cone tip that provides the ability to focus the ultrasonic energy and aim it into the anterior chamber angle. In one embodiment, the end of the tip 64 can be opened for irrigation, thereby eliminating the need for inflow port 60. In another embodiment the tip 64 may be solid to allow better ultrasonics. Preferably the tip 64 is not pointed to prevent unwanted damage to the intraocular lens or other parts of the interior of the eye.

In use, after the performance of cataract surgery and the replacement of the crystalline lens with an intraocular lens, the device 50 is used to apply ultrasonic energy into the anterior chamber angle, which is the area where the iris and cornea meet, and is directly above (as oriented in FIG. 2) the trabecular meshwork. Fluid is introduced as desired into the eye and then sonomechanical energy is transmitted to the trabecular meshwork using the device 50. The device 50 is held above the iris and intraocular lens (it preferably never contacts the iris or intraocular lens) and the ultrasonic energy is focused and directed at the anterior chamber angle, and then is moved to treat 360 degrees of the anterior chamber angle (similar to the description above with external device 10). The pulsed fluid wave vibrates the intratrabecular material free and flushes the meshwork. A coexisting aspiration port 62 allows dislodged material, such as pigment, pseudoexfoliative material, etc. in the anterior chamber to be removed.

One side effect of the method of ultrasonically vibrating the eye described herein is that the ultrasonic energy may change the vitreous gel in the back of the eye and allow vitreous detachment, i.e., separation of the vitreous gel from the retina.

It will be understood that the use of the internal device 50 is similar to the external device 10 (including frequencies, durations, power, locations, etc.), except that the internal device is used inside the eye after an intraocular lens has been implanted. The treatment may be performed on a patient directly after implantation of the intraocular lens (or directly after cataract surgery) or it may be performed on a patient that had an intraocular lens at an earlier date.

The embodiments described above are exemplary embodiments of the present invention. Those skilled in the art may now make numerous uses of, and departures from, the above-described embodiments without departing from the inventive concepts disclosed herein. Accordingly, the present invention is to be defined solely by the scope of the following claims.

What is claimed is:

1. A method of treating glaucoma in a subject's eye that includes a cornea, a sclera, a limbus and a trabecular meshwork, the method comprising the steps of:
   a. providing an ultrasonic device that emits focused ultrasonic energy;
   b. holding the ultrasonic instrument at a location external to the subject's eye;
   c. transmitting the focused ultrasonic energy at a frequency to a desired location for a predetermined amount of time; and
   d. increasing the temperature of a portion of the eye to initiate a biochemical cascade within the eye, wherein the biochemicals reduce and remove extracellular debris from the trabecular meshwork.

2. The method of claim 1, wherein the device is held against the eye.

3. The method of claim 1, wherein the device has a tip, and wherein the tip is rounded.

4. The method of claim 1 wherein steps (a) through (d) are performed at a plurality of locations about the sclera.

5. The method of claim 1 wherein the frequency is between about 20,000 Hertz and about 100,000 Hertz.

6. The method of claim 5 wherein the time is between about 5 seconds and about 45 seconds.

7. The method of claim 1 wherein the transmission of ultrasonic energy to the eye causes the tissue of the eye to be heated, wherein the heat generated is about 42.4 degrees centigrade.

8. The method of claim 1 wherein the ultrasonic device comprises a casing that includes a handle extending therefrom.

9. The method of claim 1 wherein step (d) initiates a biochemical cytokine cascade that is then absorbed systemically leading to a decrease in intraocular pressure.

10. The method of claim 1 wherein step (d) initiates heat shock proteins, stimulates matrix metalloproteinase and/or induces macrophage activity.

11. The method of claim 1 wherein step (d) includes increasing the temperature of a portion of the eye to cause an inflammatory reaction, wherein the inflammatory reaction initiates the biochemical cascade within the eye.

\* \* \* \* \*